US009616237B2

(12) United States Patent
Pare et al.

(10) Patent No.: US 9,616,237 B2
(45) Date of Patent: Apr. 11, 2017

(54) SYSTEMS, DEVICES, AND METHODS FOR SELECTIVELY LOCATING IMPLANTABLE DEVICES

(71) Applicant: EBR Systems, Inc., Sunnyvale, CA (US)

(72) Inventors: Mike Pare, San Carlos, CA (US); David Moore, San Carlos, CA (US); N. Parker Willis, Atherton, CA (US)

(73) Assignee: EBR SYSTEMS, INC., Sunnyvale, CA (US)

( * ) Notice: Subject to any disclaimer, the term of this patent is extended or adjusted under 35 U.S.C. 154(b) by 0 days.

(21) Appl. No.: 14/041,202

(22) Filed: Sep. 30, 2013

(65) Prior Publication Data

US 2014/0094891 A1  Apr. 3, 2014

Related U.S. Application Data

(60) Provisional application No. 61/707,302, filed on Sep. 28, 2012.

(51) Int. Cl.
*A61N 1/37* (2006.01)
*A61N 1/375* (2006.01)
*A61N 1/372* (2006.01)

(52) U.S. Cl.
CPC .............. *A61N 1/37* (2013.01); *A61N 1/3756* (2013.01); *A61N 1/37205* (2013.01); *A61N 1/37217* (2013.01); *A61N 1/37229* (2013.01); *A61N 1/37252* (2013.01)

(58) Field of Classification Search
None
See application file for complete search history.

(56) References Cited

U.S. PATENT DOCUMENTS

| 7,558,631 | B2 | 7/2009 | Cowan et al. |
|---|---|---|---|
| 7,606,621 | B2 | 10/2009 | Brisken et al. |
| 7,610,092 | B2 | 10/2009 | Cowan et al. |
| 8,364,276 | B2 | 1/2013 | Willis |
| 2002/0065539 | A1 | 5/2002 | Von et al. |
| 2006/0058850 | A1 | 3/2006 | Kramer et al. |
| 2006/0241714 | A1 | 10/2006 | Conley et al. |
| 2008/0294208 | A1* | 11/2008 | Willis ................ A61N 1/37235 607/3 |
| 2008/0319506 | A1* | 12/2008 | Cauller .......................... 607/46 |
| 2010/0066500 | A1* | 3/2010 | Ljungstrom et al. ........ 340/10.1 |
| 2011/0004269 | A1 | 1/2011 | Strother et al. |
| 2012/0203306 | A1* | 8/2012 | Sarvazyan ..................... 607/61 |

FOREIGN PATENT DOCUMENTS

WO  WO 2008/111998 A1  9/2008

OTHER PUBLICATIONS

International search report and written opinion dated Dec. 27, 2013 for PCT/US2013/062766.
European search report and search opinion dated Mar. 29, 2016 for EP Application No. 13842369.4.

* cited by examiner

*Primary Examiner* — Erica Lee
(74) *Attorney, Agent, or Firm* — Wilson, Sonsini, Goodrich & Rosati

(57) ABSTRACT

Method and systems for determining the location or identify of implantable devices are disclosed. An implantable device generates an electrical output and then modifies the output at a pre-configured interval for a pre-configured period. A sensor detects the modified output and locates or identifies the implantable device based on the modified output.

26 Claims, 11 Drawing Sheets

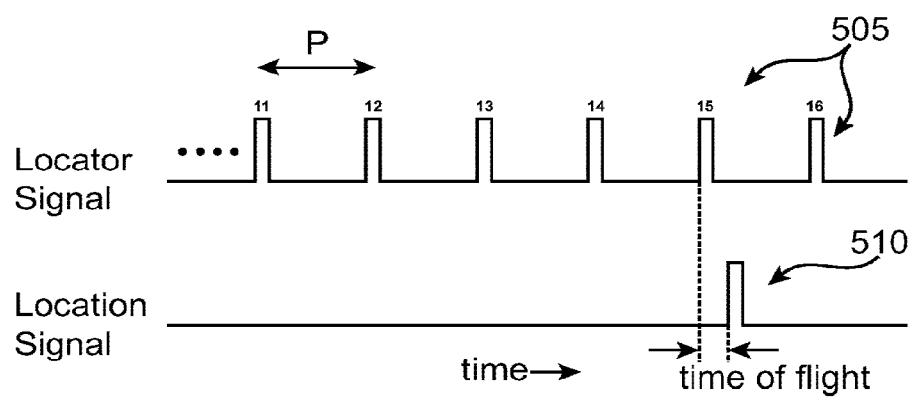
FIG. 6A
FIG. 6B
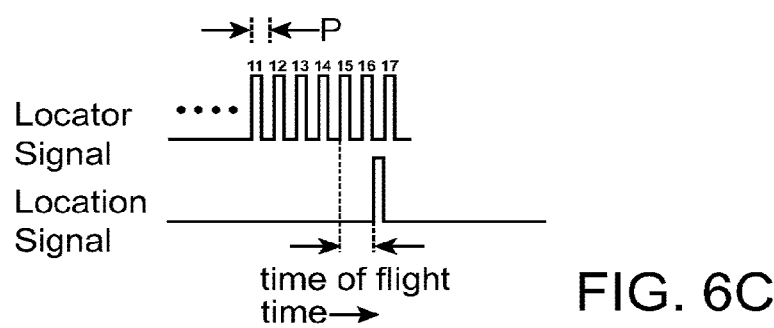
FIG. 6C
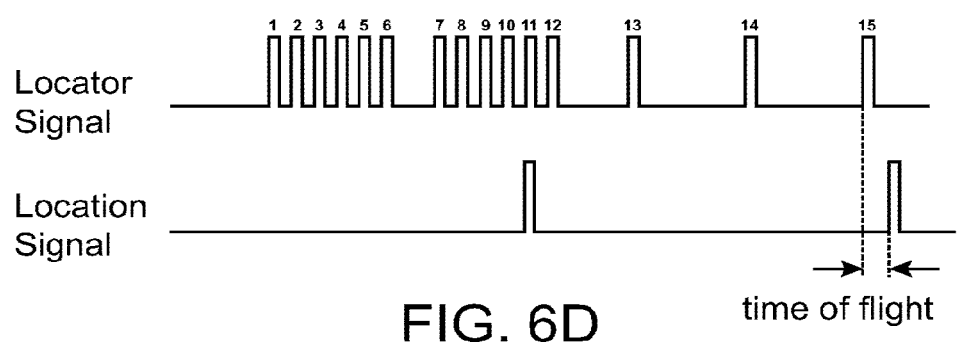
FIG. 6D

SYSTEMS, DEVICES, AND METHODS FOR SELECTIVELY LOCATING IMPLANTABLE DEVICES

CROSS-REFERENCE TO RELATED APPLICATIONS

This application claims the benefit of Provisional Application No. 61/707,302, filed Sep. 28, 2012, the entire content of which is incorporated herein by reference.

FIELD OF THE INVENTION

Present disclosure generally relates to leadless pacing and more particularly to leadless pacing with multiple receiver-stimulators.

DESCRIPTION OF THE RELATED ART

Stimulation of cardiac tissue using a leadless cardiac stimulation system has been disclosed earlier by the applicant. Generally, such a system comprises an arrangement of one or more acoustic transducers, and associated circuitry, referred to as a controller-transmitter, and one or more implanted receiver-stimulator devices. The controller-transmitter generates and transmits acoustic energy, which is received by the receiver-stimulator, and the receiver-stimulator in turn converts the acoustic energy into electrical energy, which is delivered to the tissue through electrodes.

The controller-transmitter may be externally coupled to the patient's skin, but will usually be implanted, requiring that the controller-transmitter have a reasonable size, similar to that of implantable pacemakers, and that the controller-transmitter be capable of operating for a lengthy period, typically three or more years, using batteries. The small size and long operational period require that the system efficiently utilize the acoustic energy from the controller-transmitter with minimal dissipation or dispersion of the transmitted energy and efficient conversion of the energy by the receiver-stimulator.

Briefly, in its simplest form, the receiver-stimulator comprises one or more acoustic piezoelectric receiver elements, one or more rectifier circuits, and electrodes. The piezoelectric receiver elements harvest energy from the acoustic field generated by the controller-transmitter and convert it into electric energy in the form of an AC voltage on the elements. If applied directly to the tissue this AC electrical energy does not stimulate the tissue because its frequency is too high for excitation/stimulation. In order to initiate a paced heartbeat, or provide other therapeutic stimulation to tissues, the rectifier circuits adapt all or some of the available AC electrical energy to an appropriate electrical output that is applied to the cardiac tissue through the electrodes. The acoustic field is generated and transmitted either by an externally placed or an implantable controller-transmitter that is remote from the location of the receiver-stimulator.

The acoustic energy generated by the controller-transmitter is generally referred to as an acoustic beam or ultrasound beam and is characterized by acoustic intensity (I) expressed as Watts/square meter. In order to create an acoustic intensity of Io over an area Ao the controller-transmitter must expend at least Io*Ao Watts of power. Only the portion of this acoustic beam that intersects the receiver-stimulator will be available to convert to electrical energy. If the area Ao is larger than the cross sectional area or aperture of the receiver Ar, then the ratio Ar/Ao represents that fraction of the energy in the acoustic beam that is available to the receiver-stimulator. Therefore the optimally efficient acoustic beam is very narrow and only intersects the acoustic piezoelectric receiver elements of the receiver-stimulator.

The controller-transmitter has one or more piezoelectric transducers that convert electrical energy into acoustic energy creating the acoustic beam that is directed at the receiver-stimulator. The ability of the controller-transmitter to generate this acoustic beam over a small area is characterized by its focal or directivity gain. In general the larger the cross sectional area (referred to as the aperture) of the controller-transmitter transducers, the higher the directivity gain will be. This requires the controller-transmitter to have a wide aperture transmitter that focuses acoustic energy at the receiver-stimulator. It also requires the controller-transmitter to steer or direct the acoustic beam at the receiver-stimulator. This can be accomplished by using a phased array that uses beam-forming techniques to steer the acoustic beam at the receiver-stimulator. Steering can be accomplished by adjusting the phases and amplitudes of the electrical drive signals to the transducer array, which results in adjusting the direction and focal distance of the transmitted beam.

If the location of the receiver-stimulator or the controller-transmitter does not change over time, the controller-transmitter could be configured at the time of implant to optimally select a focused beam profile that targets the receiver-stimulator location determined at the implantation time. However, in the case of the leadless system, the receiver-stimulator can be expected to move due to cardiac motion, breathing, body orientation, physiologic changes, or migration. Moreover, the controller-transmitter may move slightly due to body orientation, body movements, physiologic changes, or migration. Therefore, to accommodate the movement of the controller-transmitter and the receiver-stimulator, inventors herein have realized that successful operation in the simplest implementation would require a relatively broad beam acoustic emission. However, in this mode of operation most of the transmitted acoustic energy may pass by the receiver-stimulator and not be used efficiently. Hence, inventors herein have further realized that to improve efficiency the transmit beam needs to be significantly sharpened or focused, and reliable operation would require continuous, specific knowledge of the location of the receiver-stimulator.

For the above reasons, it would be desirable to provide a leadless system that efficiently transmits and receives acoustic energy. It would also be desirable for the transmitted beam to be adjusted, to be as focused as possible as it intersects the receiving element(s) of the receiver-stimulator. It would be particularly desirable if the location of the receiver-stimulator can be determined by the controller-transmitter, and, thereby, a focused acoustic beam could be targeted and transmitted toward the receiver-stimulator. It would also be desirable if multiple and separate receiver-stimulators can be selectively located. It would also be desirable if a receiver-stimulator is targeted and located using mechanisms that minimize the size and complexity of the receiver-stimulator such that energy utilization is not imposed upon the receiver-stimulator.

Furthermore, when multiple receiver-stimulators are used, it is important to be able to uniquely target each receiver-stimulator. Doing so enables the leadless pacing system to selectively and independently stimulate with the receiver-stimulators. It would therefore be desirable to provide a leadless system capable of accurately identifying receiver stimulator locations.

SUMMARY OF THE INVENTION

Systems, devices, and methods are provided for selectively locating implantable devices.

In one aspect, an implantable device modifies an electrical output with a glitch by a glitch generator within the implantable device. The glitch generator generates the glitch by modifying the output. The glitch occurs at a pre-configured interval and lasts a pre-configured duration. Implantable devices are constructed with known interval and duration characteristics. In one aspect, a detector senses the modified output. In another aspect, the detector sends a focused locator signal to a specific location attempting to target the implantable device.

In another aspect, a second implantable device modifies a second electrical output with a glitch by a second glitch generator within the second implantable device. The second glitch generator generates the glitch by modifying the second output. The glitch occurs at a pre-configured interval and lasts a pre-configured duration. The detector detects the second modified output and based on the characteristics of the electrical output the detector may distinguish the locations of the implantable devices based on the first glitch and the second glitch. The distinguishing may comprise analyzing presence, absence, or timing information of the first glitch and the second glitch. The detector may select the location of one of the two implantable devices based on the distinguished glitches and transmit focused energy to the selected implantable device at an intensity and duration intended to stimulate tissue with the electrical output of the selected implantable device.

In another aspect, the implantable devices may be acoustic receiver-stimulators configured to harvest acoustic energy and convert the acoustic energy to electrical output. The receiver-stimulator comprises at least two electrodes configured to transmit the electrical output to a body region. The detector may be an implantable controller-transmitter or part of the controller-transmitter and configured to transmit focused acoustic energy toward a specific location attempting to target an implantable device. The pre-configured interval occurs after the receiver-stimulator begins harvesting the acoustic energy generated by the controller-transmitter.

In yet another aspect, the implantable device comprises at least two electrodes to deliver an electrical output to the body and a glitch generator configured to modify the output. The glitch may communicate state information of the implantable device.

In another aspect, the implantable device may be configured to receive and distinguish a locator signal generated by the detector based on signal characteristics of the locator signal such as intensity or duration. Upon distinguishing the locator signal, the implantable device is configured to generate the electrical output modified by the glitch. The implantable device may also be configured to receive other signals distinguishable from locator signals and upon receiving the distinguishable signal, generate an electrical output that is not modified by the glitch generator. The detector may comprise at least one sensor configured to detect the electrical output with the generated glitch and a processor configured to analyze the electrical output to distinguish characteristics of the glitch.

This and other aspects of the present disclosure are described herein.

BRIEF DESCRIPTION OF THE DRAWINGS

The invention has other advantages and features which will be more readily apparent from the following detailed description of the invention and the appended claims, when taken in conjunction with the accompany drawings, in which:

FIGS. 6A-6D show methods for minimizing scan time for target detection.

DETAILED DESCRIPTION

Figure 1:
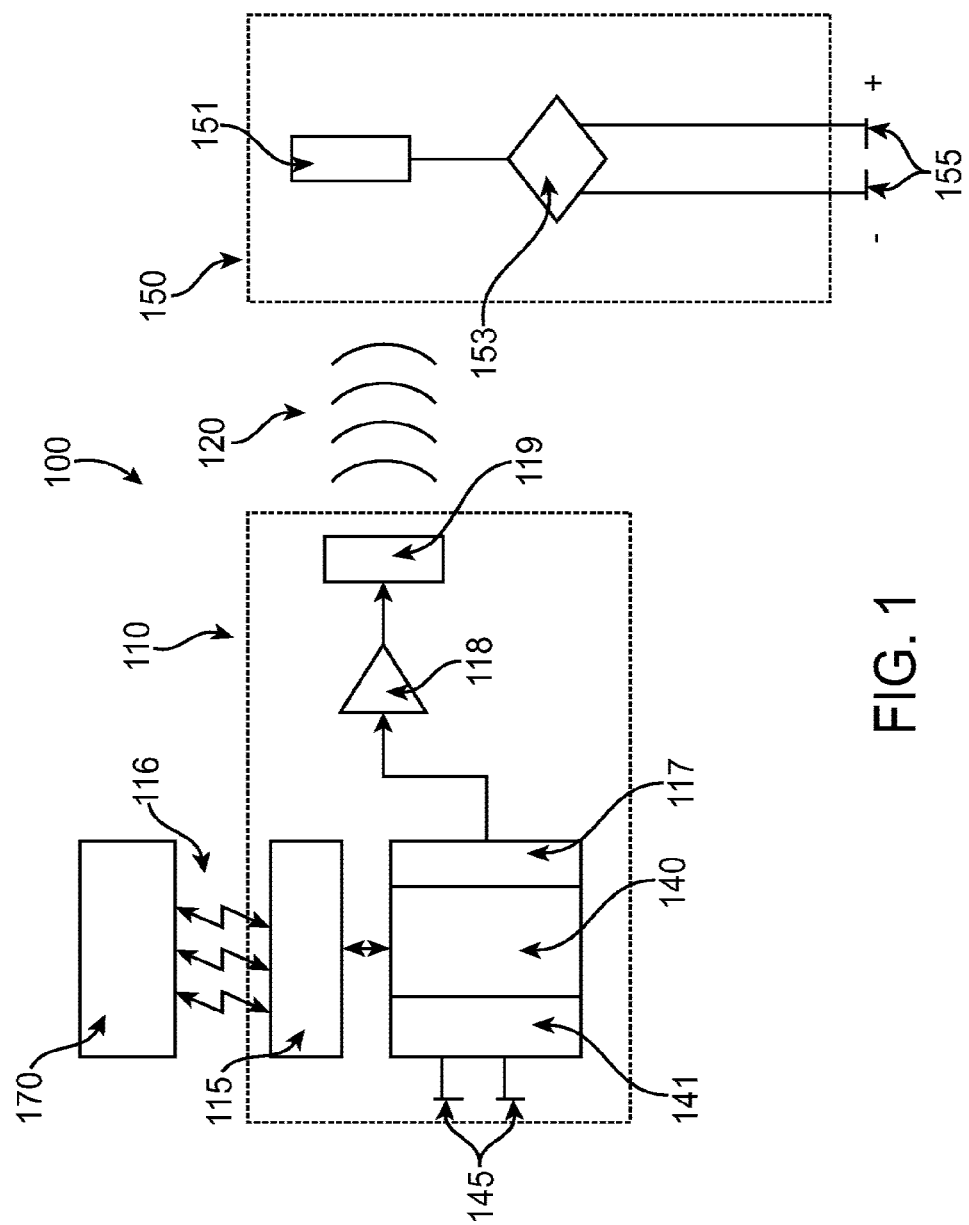
FIG. 1 is a block diagram illustrating a tissue stimulation system.

A leadless tissue stimulation system is shown in FIG. 1 as system 100. An implantable or external controller-transmitter module 110 generates acoustic waves 120 of sufficient amplitude and frequency and for a duration and period such that the receiver-stimulator module 150 electrically stimulates tissue. An external programmer 170 wirelessly communicates with an implantable controller-transmitter module 110, typically by radio frequency telemetry means 116, to adjust operating parameters. The implantable controller-transmitter module comprises a telemetry receiver 115 for adjusting the transmit acoustic characteristics, control circuitry 140 and signal generator 117, a power amplifier 118, and an output transducer assembly 119 for generating the acoustic beam 120 transmitted to receiver-stimulator 150. Understandably, the controller-transmitter 110 transmits acoustic energy to the receiver-stimulator 150 leadlessly. Control circuitry 140 contains an electrical signal sensing circuit element 141 connected to one or more sensing electrodes 145 disposed on the outer casing of the controller-transmitter or connected via cables to the controller-transmitter. Alternatively, electrical sensing circuit 141 may be an electrogram sensing circuit or may be an electrical spike detection circuit or may be an electrical glitch detection circuit.

The receiver-stimulator 150 comprises a piezoelectric acoustic energy harvesting transducer 151, rectifier circuitry 153, and tissue contacting electrodes 155. In this embodiment, acoustic energy harvested and rectified by the receiver-stimulator is directly applied to the electrodes 155. Alternatively, the receiver-stimulator module may comprise multiple transducer/rectifier channels in a variety of combinations, which may be in series or parallel orientations, or the construction may perform impedance matching, and/or for signal filtering as previously disclosed in co-pending application Ser. No. 11/315,524, to increase the efficiency of the receiver-stimulator.

Figure 2A:
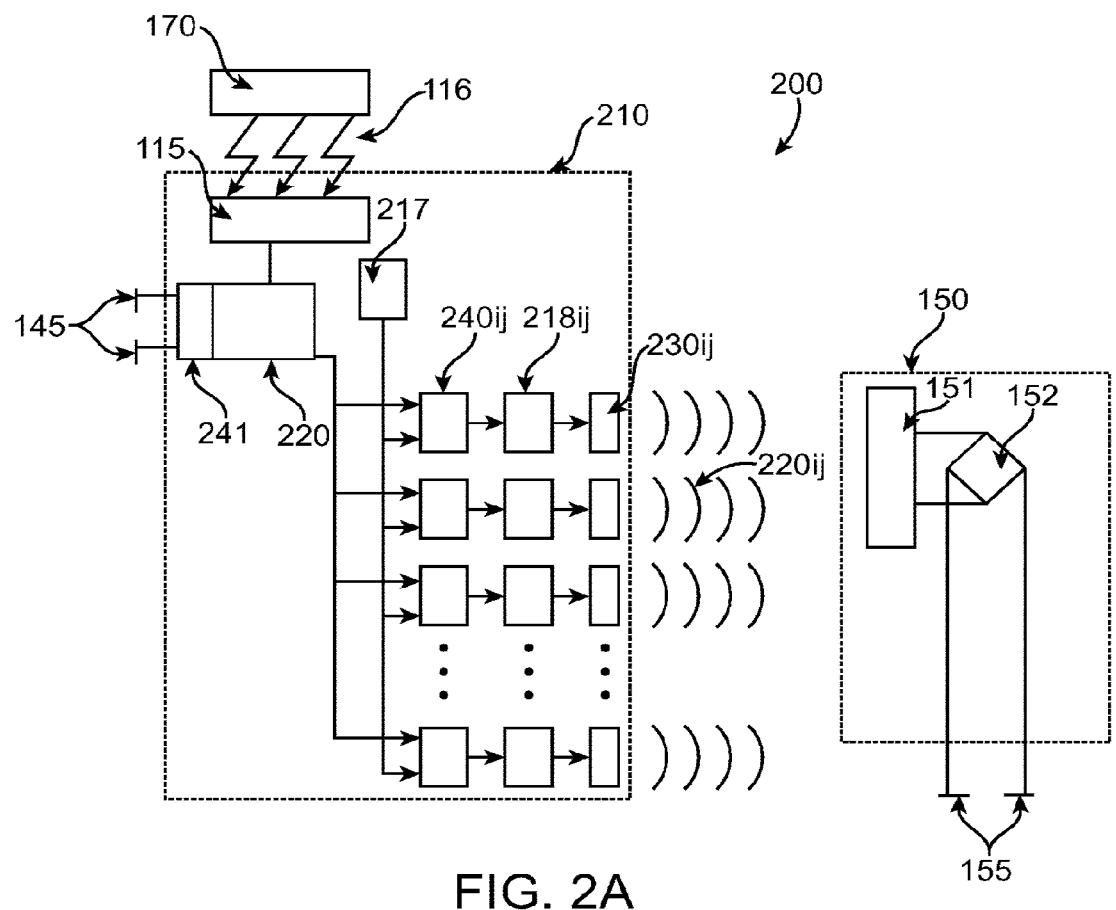
FIGS. 2A-B illustrate one embodiment of this invention.
Figure 2B:
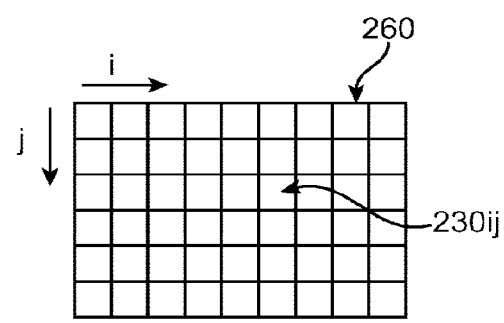

One embodiment of the present invention is shown in FIG. 2A as system 200. The controller-transmitter module 210 is placed either inside the body, but remote from myocardial tissue, or outside the body in contact with the body surface. The external programmer 170 communicates with the controller-transmitter module, typically by radio frequency telemetry 116. The telemetry module 115 inside the controller-transmitter unit 210 provides two-way communications directly with the control circuitry 220. A separate continuous wave (CW) signal generator 217 inside the controller-transmitter 210 provides the acoustic operating frequency for the system. The control circuitry 220 and signal generator 217 are both connected to each channel of a two dimensional acoustic transducer array 260 (shown in FIG. 2B), where each channel comprises a transducer element 230$ij$, a power amplifier 218$ij$ and phase shifter module 240$ij$. The phase shifter module 240$ij$, ensures that during acoustic transmissions, each channel transmits with the correct phase so as to form an efficient, focused narrow acoustic beam intended to precisely intercept the receiver-stimulator. A control signal from control circuitry 220 defines the transmit phases. The output of the phase shifter 240$ij$ then passes to the power amplifier 218$ij$ of the channel, which is also under the control of the control circuitry 220, and which can be either in an OFF state, a full ON state, or at selected levels of intermediate power which might be required for beam shading. The output of the power amplifier passes directly to the transducer element 230$ij$. One embodiment of using the phase shifter for each output channel has been described above. Other techniques can also be employed, such as direct formatting of the transmit beam by the control circuitry 220.

The controller-transmitter 210 would sample a spatial region by sending a focused, directed acoustic beam (the locator signal) to a selected portion of the region, anticipating a response (the location signal), from a receiver-stimulator 150. Any or all portions of the acoustic beam may intersect the receiver-stimulator 150. The receiver-stimulator harvests any acoustic energy impinging on it, converts the acoustic energy to electrical energy and delivers the electrical energy as an electrical output to the electrodes 155. This electrical output is an electrical signal (the location signal) that is detected by sensing electrodes 145 and electrical sensing circuits 241 of the controller-transmitter 210. Then, the controller-transmitter would adjust the focused, directed beam to target another selected portion of the region where the receiver-stimulator may be located, possibly chosen to be close to the previous region, and send the locator signal. Repeating this process thereby scans the spatial region iteratively. In this manner, electrical signals will be generated and sensed if the receiver-stimulator is in or near the portion of the spatial region being scanned. If the controller-transmitter does not sense a location signal within a reasonable time frame, the inference would be that the directed acoustic beam did not intersect the receiver-stimulator in the selected portion of the region, hence the directed acoustic beam was "off target." Such time frames may be predetermined or determined based on location signal characteristics. Alternatively, the controller-transmitter could analyze characteristics of the sensed electrical signals from one or more scans to determine the portion of the spatial region where the directed acoustic beam was adequately targeting the receiver-stimulator. The controller-transmitter then uses the focused, directed beam parameters that resulted in adequately targeting the receiver-stimulator as the target (transmission region) for the efficient transmission of acoustic energy towards the receiver-stimulator.

Figure 3:
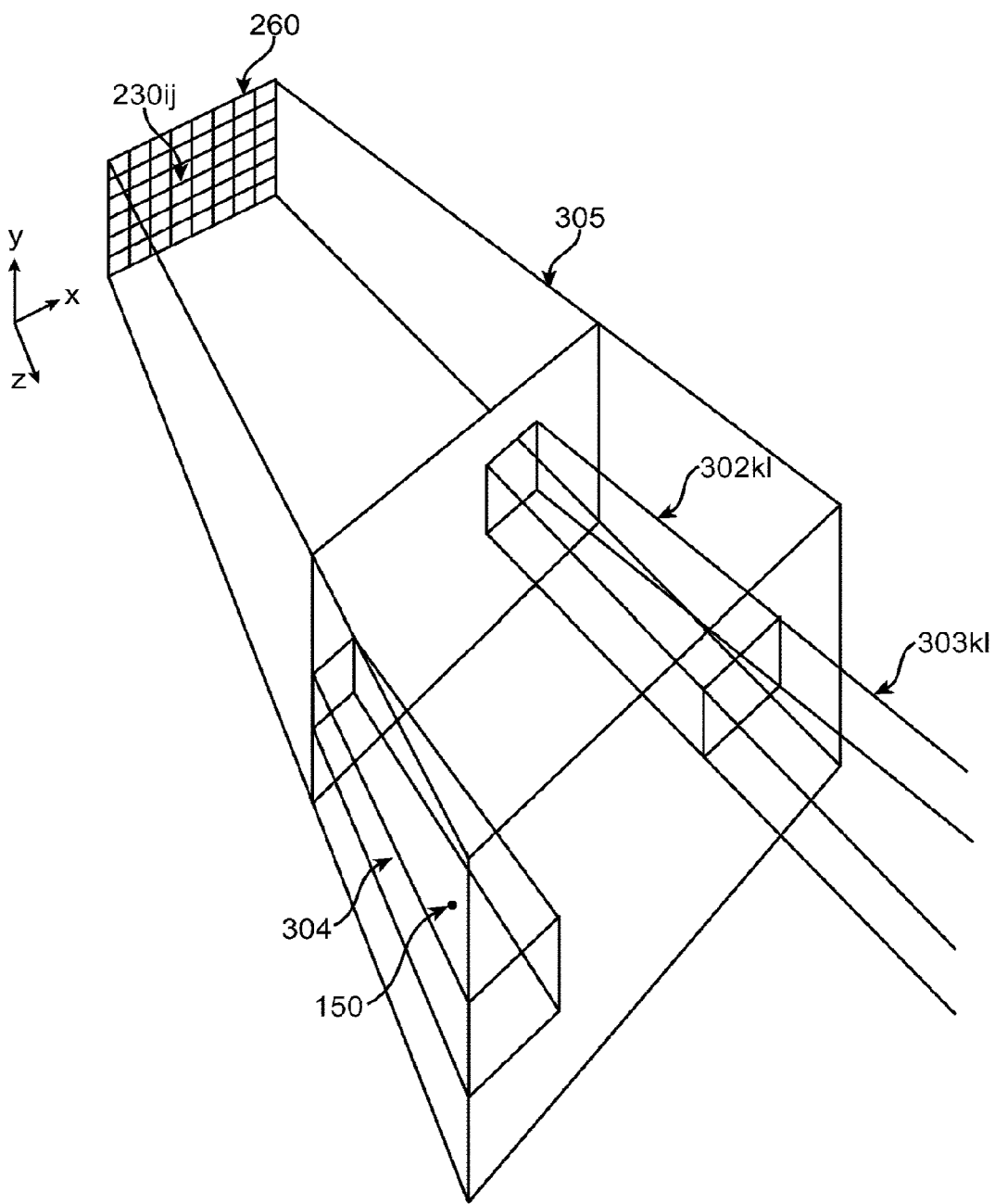
FIG. 3 illustrates the acoustic array scanning a region for location signals in response to locator signals.

The scanning process is shown in more detail in FIG. 3. The phased array 260 of the controller-transmitter is composed of individual transducers 230$ij$. For convenience the array is oriented in the x-y plane at z=0. The spatial volume to be scanned 305 encompasses possible locations for the receiver-stimulator, and, again for convenience, is located in the z>0 half space with respect to the phased array 260. The extent of 305 is constrained by anatomical limits and may vary depending on the specific stimulation application. The spatial volume 305 is broken up into multiple volumes 302$kl$, which are individually scanned or tested. The volumes 302$kl$ may or may not overlap; however, it is desirable to have the entire collection of volumes cover the region 305. The array targets a volume 302$kl$ by setting the appropriate phase parameters for the array elements 230$ij$.

The following method, provided as an example, can be used for determining the correct phase parameter for each of the array elements. A spatial location v1 for the volume 302$kl$ is picked; it is typically, but not necessarily, the center of the volume. A spatial location v2 for the array element 230$ij$ is chosen; typically, but not necessarily, the center of the array element. Note in general that v1 and v2 are 3D vectors with x, y and z components. The phase is given by $$\phi = \left(2\pi \frac{\|v1 - v2\|_2}{\lambda}\right) \mod 2\pi \qquad \text{(Equation 1)}$$

where $\| \|_2$ is the standard Euclidean norm or distance function and mod is the modulo arithmetic operator and $\lambda$ is the wavelength of the acoustic wave. Alternatively, the phase parameters may not be computed modulo $2\pi$ but rather modulo $n2\pi$ where n is the maximum phase delay, in wavelengths, across elements of the array 260 when targeting the farthest angular extent of region 305. This is slightly more efficient and therefore preferred because the first cycle of the transmitted wave will be targeted at the volume 302$kl$ whereas modulo $2\pi$ phase results in the first n cycles of the transmitted wave being out of focus.

Typically the x, y width of each volume 302$kl$ will be selected as the width of the narrowest acoustic beam that is possible from the array 260. This minimal acoustic beam width w is approximated by $$w = \frac{\lambda}{D} r$$

where $\lambda$ is the wavelength of the acoustic wave, D is the lateral size of the array 260, and r is the range or distance along the z axis from the array 260 to the volume 302$kl$. Therefore, if the array 260 is rectangular, i.e., different lateral widths in the x and y dimension, then the minimal beam width and hence x and y dimensions of the volume 302$kl$ will be different. Also note that since the minimal acoustic beam width increases with range r, the volume 302$kl$ is in general wedge shaped, expanding in lateral dimension with increased range r. The acoustic beam itself tapers off from a center peak rather than ending abruptly therefore it is desirable for the volumes 302$kl$ to have some overlap, for example 50% overlap. This provides finer targeting of the receiver-stimulator and hence more efficient transfer of acoustic energy.

The maximum lateral width, W, of the interrogation region 305 is approximated by $$W = \frac{\lambda}{d} r$$

where λ is the wavelength of the acoustic wave, d is the lateral size of an individual array element 230*i*, and r is the range or distance along the z axis from the array 260 to the volume 302*kl*. Similar to the individual volumes 302*kl* the entire scan region 305 has a wedge shape expanding out in lateral dimension with increasing range r.

If 305 lies entirely in the far field of the array 260 then depth or z focusing is not required and each volume 302*kl* can be extended over the entire z depth of region 305. However, if 305 overlaps with the near field transmission region of the phased array 260, multiple layers of volumes 302*kl*, 303*kl*, etc. must be scanned in the z dimension as well. Generally speaking, the boundary between the near and far field regions is given by $$r = \frac{D^2}{4\lambda}$$

Of course, in situations where the possible target location region is either in the far field or moves only within a fixed focal zone, then scanning in the z dimension may not be required.

Another method for quickly and efficiently determining the required phasing for the elements of the transmit array in the controller-transmitter is described below. As described previously, the required phasing can be calculated; however, this is computationally expensive, which consumes valuable energy and time, particularly because it involves the calculation of a square root. One alternative is to pre-compute the required phases for each element 230*ij* of the array 260 for each scan location 302*kl*. This, however, quickly results in a significant amount of required memory. There is the additional burden of the time required to read the phases out of memory and load them into the phase shifter 240*ij* for each of the array elements 230*ij*. This time can be reduced by increasing the clock speed of the digital electronics in the controller-transmitter or paralleling the loading process.

Figure 4:
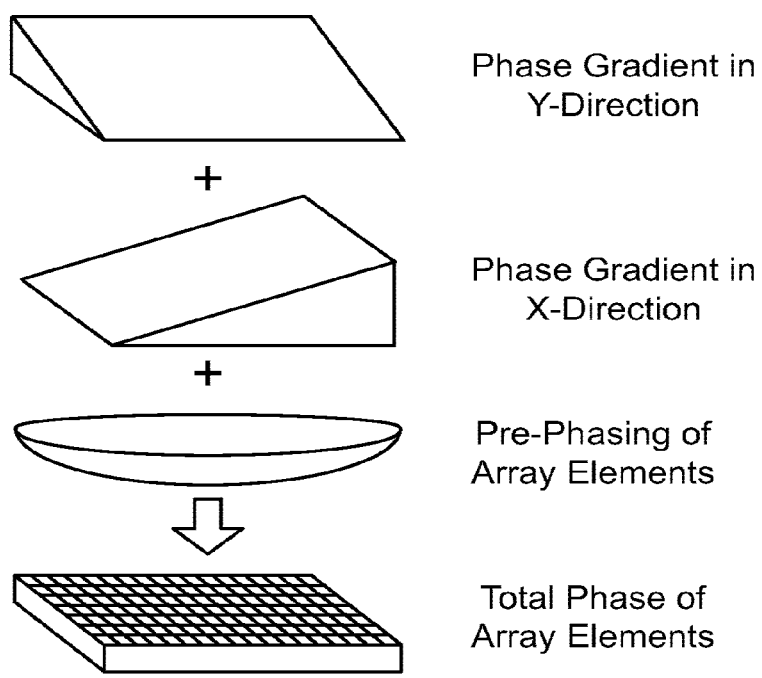
FIG. 4 shows the phases resolved into different components.

FIG. 4 describes how the required phases can be broken down into three separate components. The first two are phase gradients in the x and y direction. These are linear functions of the x and y location of the array elements and hence are relatively inexpensive to compute.

If the receiver-stimulator is very far away from the controller-transmitter only these first two components of the phase are required. However, if the receiver-stimulator is around the border region of the far-field of the array and certainly if it is within the near field, a third component shown as the pre-phasing component is required. This pre-phasing component is not a linear function of the position of the transmit element within the array and is therefore more expensive to compute.

The basic scheme is to calculate the pre-phasing component infrequently and to compute the linear component of the phases whenever the array needs to be steered to a new location. Several options exist for determining the pre-phasing component. One is to calculate the pre-phasing as the phase required to steer to a centered target (directly perpendicular, no off angle-steering) at a nominal expected range (distance) between the controller-transmitter and the receiver-stimulator. This can be done using the equation (Equation 1) shown above. The pre-phasing compensates for the fact that the receiver-stimulator is not strictly in the far-field, which is only true if it is infinitely far away from the controller-transmitter. If it were in the far-field the pre-phasing component would simply be zero, i.e., all elements in the array transmitting with the same phase. These pre-phases can be calculated and stored in read-only memory (ROM) and downloaded as part of the manufacturing of the controller-transmitter or alternatively determined once when the controller-transmitter is implanted. The latter scheme has the advantage of more exact knowledge of the range between the controller-transmitter and receiver-stimulator.

The linear phase gradients can be computed by the control circuitry and then downloaded to each of the phase controllers 241*ij* or the phase controllers can determine the linear phase components using either a look up table or dedicated computation circuitry.

Another alternative is to calculate the pre-phasing based on the nominal location of the receiver-stimulator (i.e., not just the range but also the angular location). This works well if the receiver-stimulator is located at a significant angle from perpendicular to the controller-transmitter. If there is not significant movement of the receive-stimulator relative to the controller-transmitter, the pre-phasing component only needs to be computed once saving significant computational overhead.

The electrical output produced through electrodes 155 as part of the scanning process may be considered a stimulation or pacing output, if sufficient energy is contained in the output to excite the tissue adjacent to electrodes 155; however, it is not required that the tissue be stimulated to sense the electrical signal at electrodes 145. In fact, it is advantageous for the electrical output to not be a stimulating pulse because the energy required to produce an electrical output that is detectable by electrodes 145 and detection circuits 241 is significantly lower than the energy required to stimulate tissue. This lower energy requirement is primarily achieved by shortening the duration of the locator signal and thus the resulting electrical output at electrodes 155 is typically, significantly below that used to stimulate tissue. For example, signal durations for cardiac tissue stimulation are in the range of 200 μs to 2000 μs, while typical durations are in the 400 μs to 500 μs range. The minimal duration of a locator signal is affected by various parameters: the operating frequency of the system, the Q of both transmitter and receiver transducers as well as the size of the transmit array and overall receiver structure if it contains multiple transducers. A minimal time of 10 cycles is a reasonable estimate. For an ultrasound system operating in the 500 kHz to 1 MHz frequency range this sets the minimum locator signal duration at 10 to 20 μs—at least 20 times shorter than the typical duration for tissue stimulation. This results in at least 20 times less energy used for transmitting the locator signal than that used to stimulate the tissue, making this embodiment attractive.

Short duration locator signals require different sensing circuits 241 than that used for conventional ECG processing or even pacing spike detection. ECG signals are typically processed with an amplifier bandwidth of 0.5 Hz to 100 Hz. Pacing spike detectors typically have a bandwidth of 1 kHz to 2.5 kHz. A 10-20 μs locator signal sent by the controller-transmitter would result in the receiver-stimulator delivering a 10-20 μs location signal. Sensing this location signal would require a bandwidth of up to 100 kHz.

Research on both animal models and humans indicate that it is common to observe signal attenuation of 65-80 dB for a pacing signal generated from within the heart and sensed on surface ECG electrodes. Therefore a 1 volt electrical output pulse delivered across electrodes 155 would result in a 560 microvolt to 100 microvolt signal on electrodes 145. State of the art amplifiers can achieve noise figures in the range of 20 nV/(Hertz)$^{1/2}$, resulting in noise on the order of 6 microvolts over a 100 kHz bandwidth, resulting in a very reasonable signal to noise ratio for sensing of a location signal. However, such high bandwidth, high gain amplifiers consume more power than conventional ECG amplifiers which are amplifying lower bandwidth higher amplitude signals. It is therefore advantageous to only turn on these amplifiers when they are required, i.e., immediately following transmission of acoustic locator signals.

Figure 5A:
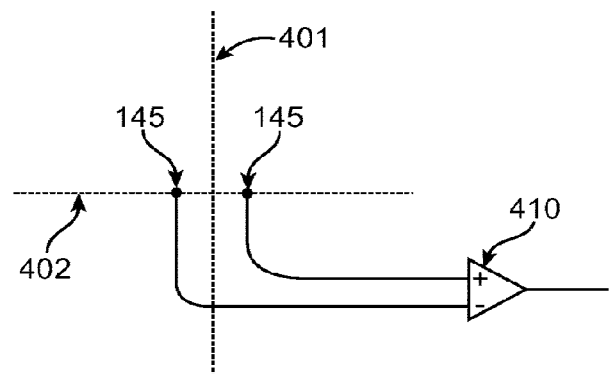
FIGS. 5A-5C show various electrode configurations.
Figure 5B:
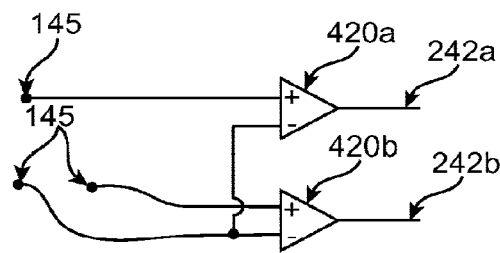
Figure 5C:
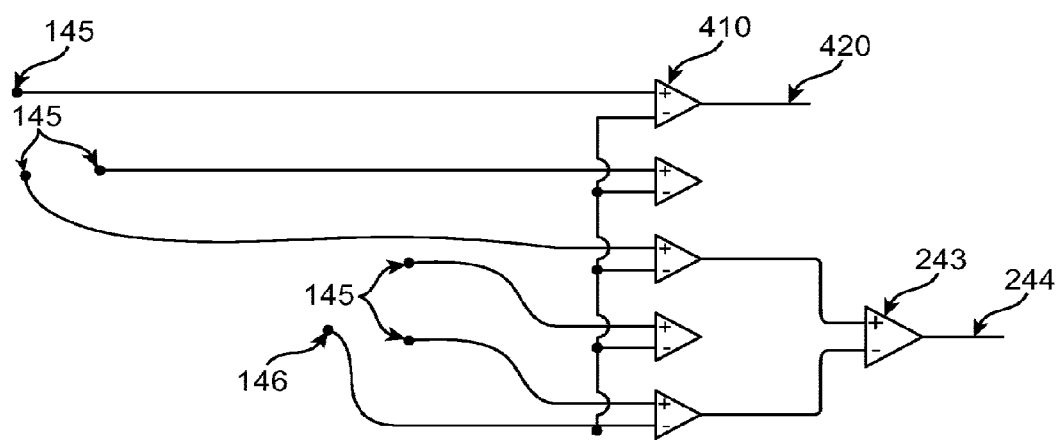

Additionally it is important to note that the location signal is generated and sensed from two electrodes that are spatially close to each other. The positions of both, receiver-stimulator electrodes 155 and controller-transmitter electrodes 145, are constrained by practical limitations. Hence, the electrical signal produced by electrodes 155 will have a dipole radiation pattern and the sensitivity of the electrodes 145 will have a dipole pattern as well. FIG. 5a shows a typical dipole arrangement. Sensing electrodes 145 are input into a differential amplifier 410. The dashed line 401 indicates a region, a "blind spot", where a signal source cannot be sensed by the electrodes 145. This is because a signal source placed along this line is equidistant to both electrodes 145 and the differential amplifier subtracts these two equal signals producing a null output. Correspondingly, the dashed line 402 indicates a region where a signal source will be sensed with maximum output from the amplifier 410. A similar behavior occurs as a result of the transmission of the electrical signal through electrodes 155. Therefore, the overall attenuation will be the result of the superposition of two dipole patterns. In order to avoid potential "blind spots" in these dipole patterns it is, therefore, advantageous to use more than two electrodes 145 on the controller-transmitter. FIG. 5b shows how the addition of a third electrode eliminates the problem of this "blind spot". Two amplifiers 420a and 420b are used to amplify signals from two separate dipoles oriented 90 degrees apart. The two signal outputs, 242a and 242b of 420a and 420b, respectively, are then analyzed for the presence of the location signal. Even more improvements can be made by the addition of more electrodes that are spatially separated from the first three electrodes as shown in FIG. 5c. This has the additional benefit of avoiding any "blind spots" in the dipole pattern generated by electrodes 155 at the receiver-stimulator. One electrode 146 is chosen as a reference and all other electrodes 145 are amplified relative to this reference using amplifiers 410i each of which produces a signal 420i. The dipole signal 244 from any pair of electrodes can then be calculated by taking the difference between two of the output signals 420i, using 243 which can be implemented either as a hardware differential amplifier or in software as the subtraction of two digitized signals. As discussed above, the amplifiers 410i are necessarily high bandwidth, high gain amplifiers and therefore consume significant power. Therefore, it is advantageous to only use those that provide the largest amplitude location signals. Assuming that the motion of the receiver-stimulator and controller-transmitter will not significantly change the amplitude of the location signal, once the electrode pair that produces the largest location signal is determined, only the amplifiers used to produce this signal need to be used, significantly reducing power consumption.

An important consideration is the time taken to determine the location of the receiver-stimulator. Obviously, this time should be as short as possible. If this time is comparable to the cardiac cycle, then motion of the heart between determination of the location and subsequent delivery of stimulation energy becomes problematic. It is also advantageous to minimize the required scan time when the receiver-stimulator is used concomitantly with a standard pacemaker to achieve therapeutic bi-ventricular pacing. In this case, as disclosed in pending application Ser. No. 11/315,023, the controller-transmitter transmits acoustic energy to stimulate the heart immediately following the detection of a right ventricular (RV) pacing artifact in the concomitantly implanted device. Preferably, the determination of the receiver-stimulator position is done after the detection of the RV pacing artifact so that the effect of cardiac motion between position determination and stimulation is minimized.

FIG. 6 shows several methods for minimizing the required scan time. FIG. 6a shows a partition of the space to be scanned into different target regions. The partition assumes there is no depth targeting and therefore the scan space is in the x-y plane at a fixed z location. The method can be easily extended to the case of depth targeting. The speed of sound in the soft tissue and blood is approximately 1.5 mm/μs. Considering a large distance between the controller-transmitter and receiver-stimulator of 200 mm results in a maximum time of flight of approximately 133 μs. FIG. 6b shows a simple scan method where the time between locator signals, P, is chosen to be greater than the expected time of flight. A method for processing the output signal 244 is described as follows. Detection of the location signal 510, following a locator signal 505, indicates that the receiver-stimulator is contained in the volume corresponding to the locator signal 505 (volume 15 in FIG. 6a). Furthermore, the time of flight which is proportional to the range between the controller-transmitter and the receiver-stimulator can be measured by the time delay between transmission of the locator signal and detection of the location signal.

FIG. 6c demonstrates a faster scanning method. In this case, the time between transmit pulses (locator signals), P, is shorter than the actual time of flight and is limited only by the duration of each individual locator signal and the setup time for the controller-transmitter to prepare for the next locator signal. This results in multiple locator signals in flight simultaneously between the controller-transmitter and receiver-stimulator, considerably reducing the scanning time. Once a location signal is detected, determination of the actual locator signal that produced the location signal requires knowledge of the nominal time of flight between the controller-transmitter and receiver-stimulator as shown in FIG. 6c. This optimized scheme is applicable if the previous location and hence time of flight to the receiver-stimulator is known and only small movements of the receiver-stimulator relative to the controller-transmitter are expected. The time between locator signals, P, can be set to the maximum expected range of motion. For example, if the maximum possible motion is 40 mm then P must be at least 40/1.5 or 27 μs.

During initial operation, when the location of the receiver-stimulator and hence nominal time of flight is totally unknown, a hybrid technique as shown in FIG. 6d can be used. A rapid scan of the entire region is performed using a technique similar to that shown in FIG. 6c until a location signal is detected. Once a location signal is detected a slower scan similar to that shown in FIG. 6b is performed for the volumes near the detected location signal (starting with volume 13 then 14, etc.) This will pinpoint the exact volume (in this case 15) and allow back calculation of the actual time of flight.

In some cases, a longer duration between locator signals than that used in FIG. 6b may be required. This can happen if there is sufficient acoustic energy from the locator signal is reflected off anatomical structures in the body and the receiver-stimulator converts these reflected locator signals. Generally, this is handled by increasing the time between locator signals such that any reverberation or reflection from a previous locator signal has decayed before transmitting another locator signal. However, the likelihood of this problem occurring can be substantially reduced by prior knowledge of the nominal time of flight. This allows the controller-transmitter to look for a location signal over a narrow time window eliminating false detections due to reflected locator signals.

Another strategy for minimizing the scan time and the energy expended on the scan itself is to perform an intelligent search. One approach is to start the scan by transmitting a locator signal to the previous known position of the receiver-stimulator. Therefore, if the receiver-stimulator has not moved outside of the scan volume, only one locator signal is required. If more scanning is required, another strategy is to expand the search out from the last known position for the receiver-stimulator. Another approach is to remember the previous history of motion of the receiver-stimulator and use this to intelligently scan for it. This will greatly reduce the number of scans whenever the primary motion of the receiver-stimulator is periodic for example due primarily to cardiac and respiratory motion.

It should be noted that more than one receiver-stimulator could be implanted and operated using the different approaches described above for optimizing energy transmission. The location of each receiver-stimulator relative to other receiver-stimulators can be registered during the time of implantation. Following implantation, when the receiver-stimulators move due to cardiac motion, breathing, etc., they are likely to move in concert with each other. However, the relative location of the receiver-stimulators with respect to the controller-transmitter, which impacts the optimal energy transmission by the controller-transmitter, is likely to change due to cardiac motion, breathing, etc. To address this issue, if the location of the first receiver-stimulator is identified using one of the approaches described above, the location of the other receiver-stimulators is immediately computed, based on the relative location of the other receiver-stimulators that was registered during implantation.

Additionally or alternatively, each receiver-stimulator (when multiple receiver-stimulators are implanted) can be selectively located using a locator signal with a unique frequency or phase. The approaches described earlier can then be used sequentially for each receiver-stimulator to optimize the energy transmission from the controller-transmitter. Or more simply, if multiple receiver-stimulators are implanted with sufficient difference in location, each could be located directly by the previously described methods, based on knowledge of previous locations and possibly relying on the relative locations between devices being unlikely to change significantly.

Figure 7A:
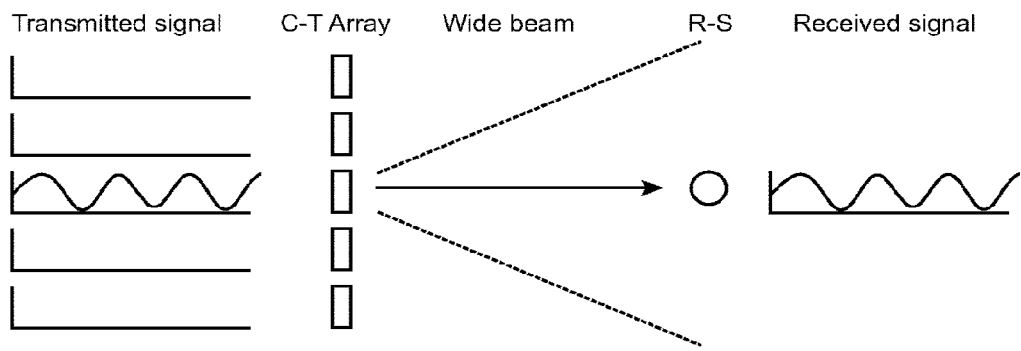
FIGS. 7A-7C illustrate an embodiment using frequency shifting for acoustic beam steering and optimizing energy transmission.
Figure 7B:
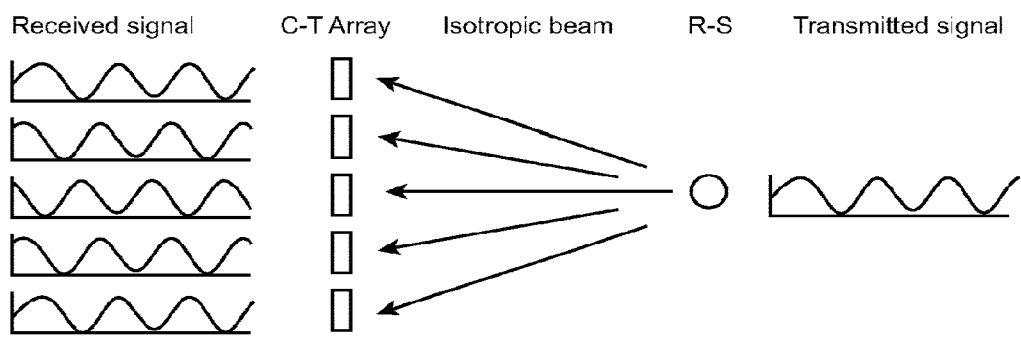
Figure 7C:
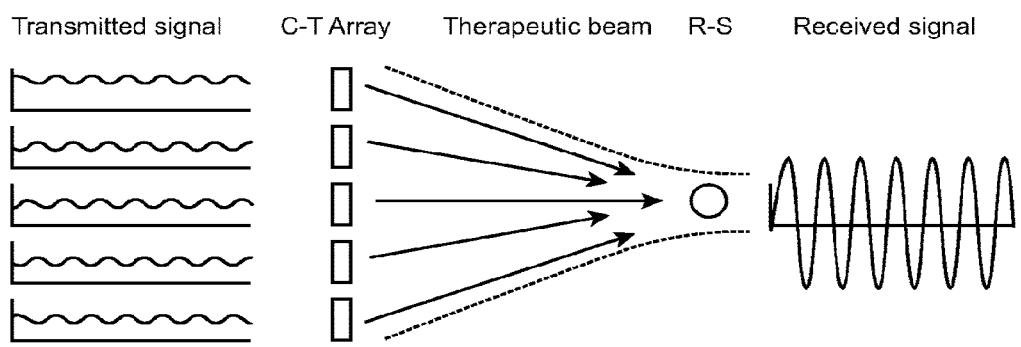

Another embodiment of the invention described herein for optimizing energy transmission from a controller-transmitter is illustrated in FIGS. 7A-7C. In FIG. 7A, one element of the controller-transmitter array ("C-T Array") transmits a wide beam acoustic burst (locator signal), which is received by the receiver-stimulator ("R-S"). As the signal is being received in the receiver-stimulator, it is frequency shifted and retransmitted isotropically back to the controller-transmitter, as depicted in FIG. 7B. This retransmission occurs as the locator signal is being received by the receiver-stimulator. The location of the receiver-stimulator with respect to each element of the C-T array is recorded into the memory of the controller-transmitter as the detected phase received per channel. Then, at the clinically appropriate time, the controller-transmitter uses the recorded phase measurements to transmit acoustic energy as a focused beam to the receiver-stimulator to be delivered to electrodes for stimulation of tissue, as shown in FIG. 7C.

The amount of energy contained in the locator signal generated from a single element in the phase measurement mode described above may be substantially greater than that used for stimulation. However, because the correct phase measurements have been obtained, significantly less energy will be transmitted for the stimulation by the entire array than would have been required to achieve the same level of energy delivered to the tissue using a wide beam. Now each element of the array would transmit a focused beam that is much more efficient, compared to the wide beam each element would have transmitted in the absence of the correct phase measurement. Additionally, in the method described above, phase measurements were obtained without additional computations, thus further minimizing the energy consumption.

Upon creation of the focused beam used for stimulation, not all elements of the array need necessarily be driven at the same amplitude. If one pathway or the other from the receiver-stimulator to the array of elements shows either more or less attenuation, this may be overcome by transmitting with either more or less energy, respectively, or by completely turning off severely impacted array elements. Further, it is well known in the art of array design, that aperture shading (lower amplitude emissions from the edges of the array) has the effect of flattening the acoustic beam, for a greater uniformity within the beam. This can also be accomplished, guided by pre-programmed computations in the controller-transmitter.

Additional aspects of the invention are described below. In one embodiment where no locator signal is required, the receiver-stimulator first receives acoustic energy from the controller-transmitter, stores part of the received energy and directs the rest to the tissue. The stored energy could be anywhere from 0 to 100%, and ideally about 5%, of the received energy. Based on a variable, fixed or periodic timeout within the receiver-stimulator, but before the next transmission of acoustic energy from the controller-transmitter, the stored energy is used by the receiver-stimulator to generate a location signal. The location signal may be an electrical signal, or it may be an acoustic transponder signal transmitted to the controller-transmitter, or a similar signal generated by the receiver-stimulator as a homing beacon to signal the location of the receiver-stimulator. The controller-transmitter senses the location signal and computes the location of the receiver-stimulator, using information, such as amplitude, phase, arrival time, or the like from the location signal. Having identified the location of the receiver-stimulator, the controller-transmitter is then able to focus the transmitted acoustic beam to the location or region of the receiver-stimulator and thereby transmit energy or exchange communication optimally.

Alternatively, the controller-transmitter transmits a locator signal in the form of sufficient acoustic energy to a passive receiver-stimulator that uses all the energy received to generate a location signal. In this embodiment the receiver-stimulator would be adapted to have a state machine that switches between using acoustic energy for location signals and using acoustic energy for functional purposes such as stimulation. The location signal is received by the controller-transmitter, which determines the location of the receiver-stimulator based on signal characteristics contained in the location signal and then generates a focused beam that is targeted at the location or region of the receiver-stimulator.

As indicated above, it should be noted that the acoustic receiver of the present invention can function as a receiver-stimulator or a receiver-converter, where the receiver-converter can act as a diagnostic tool. While the examples illustrate the receiver-stimulator embodiments, the energy optimization techniques described above are equally applicable for a receiver-converter.

While the location signal has been detailed as an electrical output signal it should be understood that the location signal may be of any nature that can be detected by a controller-transmitter. For example it could be a passive echo from the receiver-stimulator or the receiver-stimulator could be adapted to transmit an acoustic signal in response to the locator signal.

Additionally, the location signal may include additional information, including but not limited to the identification or timing information for the implantable device. In one embodiment, the location signal is an electrical output modified with a timed glitch. The modified glitch is detectable by an implantable or external detector such as an implantable controller-transmitter. The detector could then use information embedded in the location signal, including but not limited to the presence, absence, or timing information as a locator and/or as an identifier for the implantable device. Specifically, the present devices, systems, and methods may be used independently, thereby eliminating the need for an identity-assignment algorithm in the case that either their locations and/or identities were lost. Alternatively, in another embodiment the present devices, systems, and methods may be used in addition to one or more implantable device identification and communication devices, systems, and methods such as the embodiments described above or any other identity-assignment algorithm.

Figure 8:
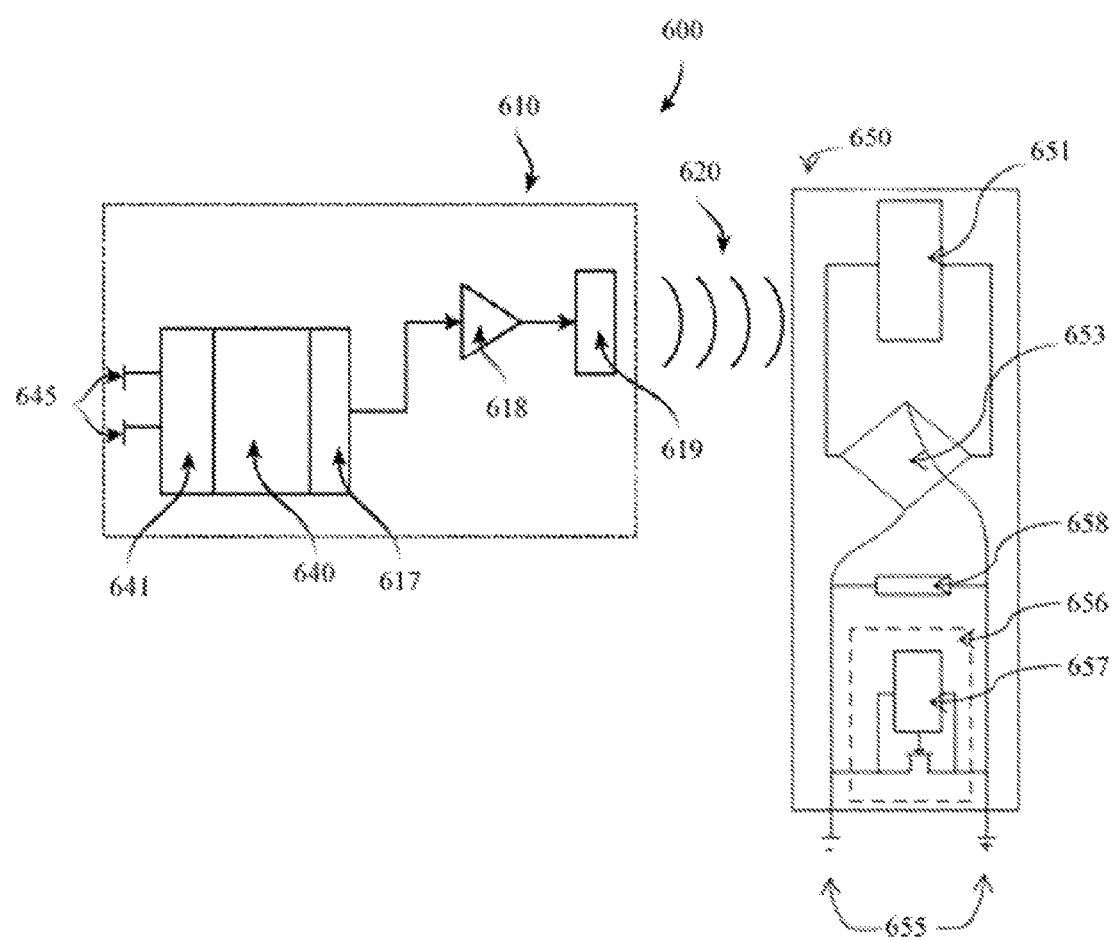
FIG. 8 illustrates an embodiment of an implantable system wherein an implantable device comprises a glitch generator.

Referring now to FIG. 8, which illustrates an embodiment of the invention wherein an implantable device 650 exemplarily shown as a receiver-stimulator is configured to produce a location signal modified with a glitch. The receiver-stimulator 650 comprises at least one receiving transducer 651, rectifier circuitry 653, a glitch generator 656, and at least two electrodes 655 configured to transmit the electrical output to a body region. In one embodiment, the electrodes 655 may be tissue stimulating electrodes.

In one embodiment, the glitch generator 656 is configured to modify an electrical output by producing a glitch as a location signal. In one embodiment, the glitch may be produced by shorting the electrical output. The shorting may occur at a pre-configured interval after the onset of incoming acoustic energy to the receiver-stimulator 650 and last a pre-configured period. In one embodiment, the glitch generator 656 comprises a timing element 657. The timing element 657 is configured to determine the delay between the start of acoustic energy incoming to the receiver-stimulator 650 and the beginning of the short. The timing element 657 may also be configured to determine the duration of the short. The timing element 657 may have various configurations with various delays before initiating the short and various durations of the short. The glitch generator 656 may be configured to allow the electrical output for a specified duration after receiving acoustic energy, short the electrical output for a specified duration, and then reopen the electrical output. In another embodiment, the glitch generator 656 is configured to initially short the electrical output and then allow the electrical output to start after a specified duration.

In another embodiment, the glitch generator 656 may be configured to modify an electrical output by producing a glitch as a location signal by using a switch. The switch may be either in series or in parallel configurations. In one embodiment the glitch generator 656 comprises a switch that is in series with the load and is nominally closed. The switch would then be opened to create a glitch in the output. In another embodiment the glitch generator 656 comprises a switch that is in the series with the load and is nominally open (disconnected from the tissue). In one embodiment, the switch is open allowing the voltage to rise without a load so it can power a timing circuitry. The switch would then be closed to deliver energy to the tissue with different timing to create glitches.

Optionally, the receiver-stimulator 650 may comprise a protection circuitry 658 to protect the rectifiers 653 from voltages exceeding a threshold as previously disclosed in co-pending application Ser. No. 12/721,483 incorporated herein by reference in its entirety. In one embodiment, the protection circuitry 658 comprises a Zener diode or a series of GaAs Schottky diodes.

It is contemplated that in one embodiment, multiple receiver-stimulators 650 may each use unique glitch generators 656 with uniquely configured timing elements 657. This improves production by allowing at least some components of multiple receiver-stimulators 650 that are uniquely locatable and identifiable to be produced in identical ways. All other parts of the receiver-stimulator 650 may be manufactured identically. In one embodiment, more than one receiver-stimulator may be used in a multi-device system. In such an embodiment, the system comprises multiple receiver-stimulators 650 with different glitch generators 656. The controller-transmitter 610 is configured to locate and/or identify a receiver-stimulator 650 based on the differences or uniqueness in the glitches produced such as differences in the timing of the glitches. A multi-receiver system may also comprise a receiver-stimulator 650 with a glitch generator 656 and a receiver-stimulator 650 without a glitch generator. In this embodiment the controller-transmitter 610 is configured to locate or identify the receiver-stimulator 650 comprising a glitch generator 656 based on the presence of a glitch. The controller-transmitter 610 is also configured to locate and/or identify the receiver-stimulator 650 without a glitch generator 656 based on the absence of a glitch. A multi-receiver system may also comprise groups of receiver-stimulators 650 with identical glitch generators 656 intended to be targeted together.

The electrical output produced through electrodes 655 as part of the location and/or identification process may be a stimulation or pacing output wherein the output is of sufficient electrical energy to excite the tissue adjacent to electrodes 655; however, it is not required that the tissue be stimulated to detect the electrical output signal at electrodes 645. In one embodiment, locator signals, such as short duration locator signals may be send wherein the duration of the locator signal has a value that is significantly below that used to stimulate tissue. The resulting electrical output at electrodes 655 would be non-stimulating.

In one embodiment the glitch generator 656 is to modify an electrical output by producing a glitch as a location signal when a non-stimulating locator signal is received. In another embodiment, the glitch generator 656 is configured to modify a location signal configured as an electrical output when acoustic energy intended to cause stimulation is received by the receiver-stimulator 650. In one embodiment, the locations and/or identities of the receiver-stimulator 650 may be confirmed with each stimulation cycle. In another embodiment, the receiver-stimulator 650 is configured to distinguish a non-stimulating locator signal from acoustic energy intended to cause stimulation. In this embodiment the glitch generator 656 would modify the electrical output upon receiving a locator signal but would not modify the electrical output if acoustic energy intended to cause stimulation is received.

In one embodiment the receiver-stimulator 650 does not require a battery or local energy storage. The receiver-stimulator 650 may be configured to passively convert acoustic energy received from the controller-transmitter 610 to an electrical output.

In one embodiment, the controller-transmitter 610 comprises control circuitry 640, a signal generator 617, a power amplifier 618, and a transducer assembly 619 for generating an acoustic beam 620 transmitted to receiver-stimulator 650. The controller-transmitter module 610 may be placed either inside the body or outside the body in contact with the body surface. The controller-transmitter 610 is configured to sense the location signal generated by the receiver-stimulator 650. In one embodiment, where the location signal is an electrical output, the control circuitry 640 is configured to contain an electrical signal sensing circuit element 641 connected to two or more sensing electrodes 645 disposed on the outer casing of the controller-transmitter 610 or connected via cables to the controller-transmitter 610. The electrical sensing circuit 641 may be one or more of an electrogram sensing circuit, an electrical spike sensing circuit, or a glitch sensing circuit. In one embodiment, the electrical signal sensing circuit element 641 is configured to sense the location signal as an electrical output and distinguish glitches incorporated within modified electrical outputs. The control circuitry 640 comprises a processor configured to analyze glitches in the electrical signal and to locate or identify receiver-stimulators 650 based on characteristics of the analyzed glitches. The processor may analyze the presence, absence, or timing of a glitch. The processor is further configured to distinguish between location signals with different glitches.

Figure 9:
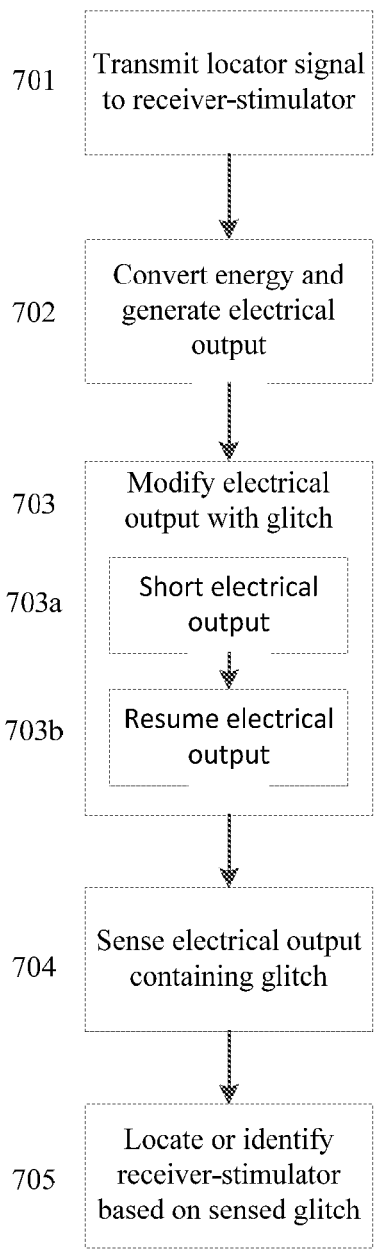
FIG. 9 is a flow diagram illustrating a process of identifying a receiver-stimulator.

FIG. 9 is a flow diagram illustrating one embodiment of a process of selectively locating and/or identifying a receiver-stimulator 650 by modifying an electrical output with a glitch as a location signal. At step 701, the controller-transmitter 610 transmits a locator signal to a receiver-stimulator 650. In one embodiment the locator signal is acoustic energy. The locator signal may be a focused acoustic beam targeted at the receiver-stimulator 650. If the location of the receiver-stimulator 650 is unknown, the controller-transmitter 610 may locate the receiver-stimulator 650 using one of the approaches described above.

At step 702, the receiver-stimulator 650 converts the acoustic energy into electrical energy and delivers a location signal, configured as an electrical output onto the electrodes 655. At step 703, the electrical output is modified by the receiver-stimulator 650 with a specifically-timed glitch. In one embodiment, the timed glitch is caused by shorting the electrical output. In such embodiment, after a pre-configured delay occurred after the start of incoming acoustic energy to the receiver-stimulator 650, at step 703a, the electrical output is shorted. The short lasts a pre-configured duration, and then at step 703b, it opens again, resuming the electrical output.

At step 704, the controller-transmitter 610 senses the modified electrical output of the receiver-stimulator 650 comprising the glitch. At step 705, the controller-transmitter 610 locates and/or identifies the receiver-stimulator 650 based on the sensed glitch. The controller-transmitter 610 may identify the receiver-stimulator 650 based on state information or signal characteristics of the glitch such as its presence, absence, or timing information. The glitch may also indicate other information about the receiver-stimulator 650 to the controller-transmitter 610 such as whether the device is functioning correctly.

If multiple receiver-stimulators are present, the location and identification process may be repeated to locate or identify additional receiver-stimulators. In one embodiment the location and identification process is repeated sequentially until a desired receiver-stimulator is located and/or identified or a group of receiver-stimulators is located or identified. In another embodiment, the process is repeated until each receiver-stimulator is uniquely located and/or identified.

Selectively locating and/or identifying the receiver stimulators allows the controller-transmitter 610 to independently control each receiver-stimulator's output and allows for specific parameters to be associated with each receiver-stimulator. In one embodiment, the controller-transmitter 610 first performs this identification process. The controller-transmitter 610 then selectively transmits additional acoustic energy for the purposes of delivering a therapeutic electrical output to one of the receiver-stimulator and not the others. In one embodiment, the controller-transmitter 610 may also selectively transmit additional acoustic energy for the purposes of delivering a therapeutic electrical output to an identified group of receiver-stimulators.

The above described location and identification process may alternatively be used to identify non-stimulating implantable devices. In this embodiment the electrical output does not stimulate the surrounding tissue.

Figure 10A:
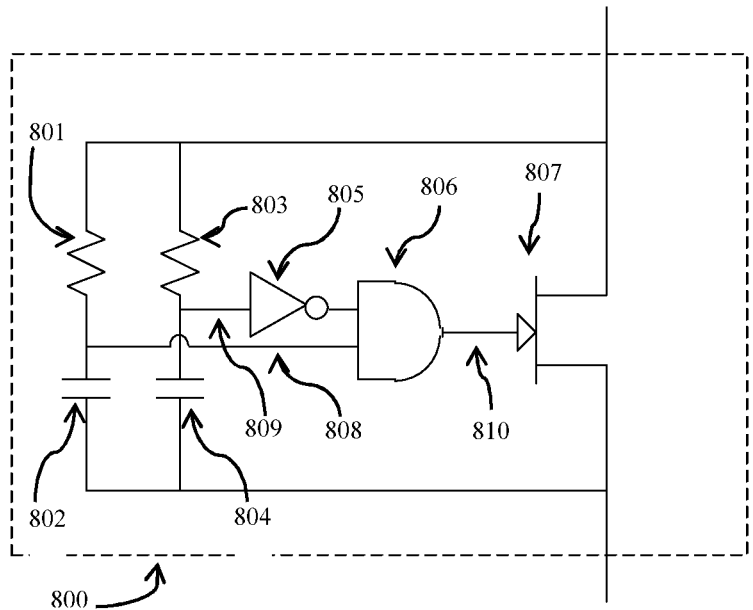
FIGS. 10A-11B show various glitch generator configurations.
Figure 10B:
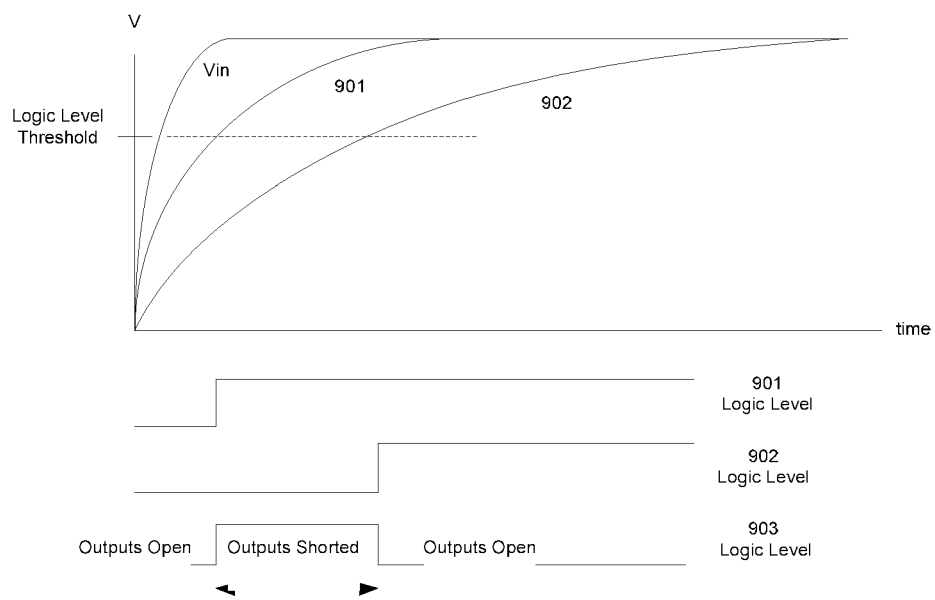

The glitch generator may have a variety of implementations. One embodiment of the glitch generator is shown in FIGS. 10A-B. This embodiment of the glitch generator 800 comprises resistors 801 and 803, capacitors 802 and 804, an inverter 805, an AND gate 806, and a field-effect transistor (FET) 807. The FET 807 may be a JFET, MOSFET or any other form of FET. As seen in FIG. 10B, initially the logic levels at 901, 902, and 903 are low. At this point the electrical output is not shorted. After a specified time from the input of acoustic energy to the receiver-stimulator, voltage at 901 crosses the logic level threshold and the logic level of 901 becomes high. The logic level at 902 is still low. The logic level at 903 is now high and the electrical output is shorted. After another specified time the voltage at 902 crosses the logic level threshold and the logic level at 902 becomes high. At this point the logic level at 903 returns to low and the short opens.

Figure 11A:
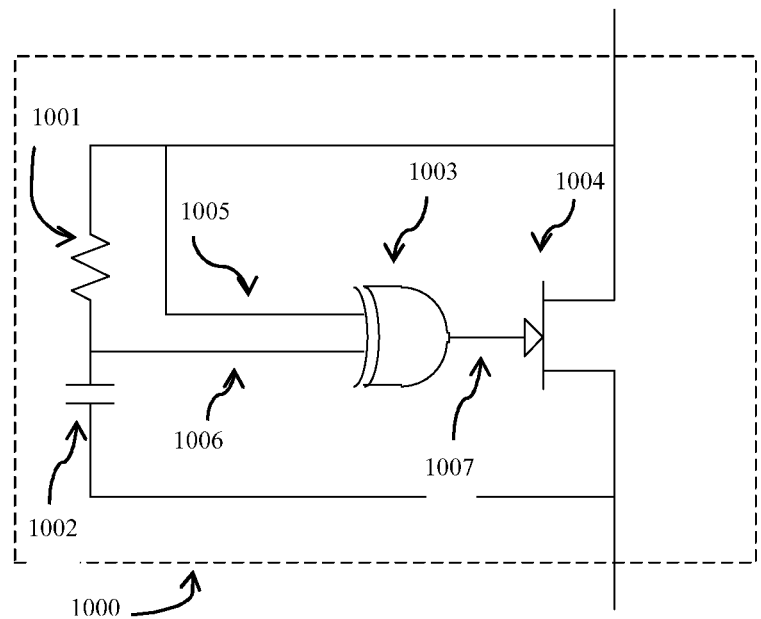
Figure 11B:
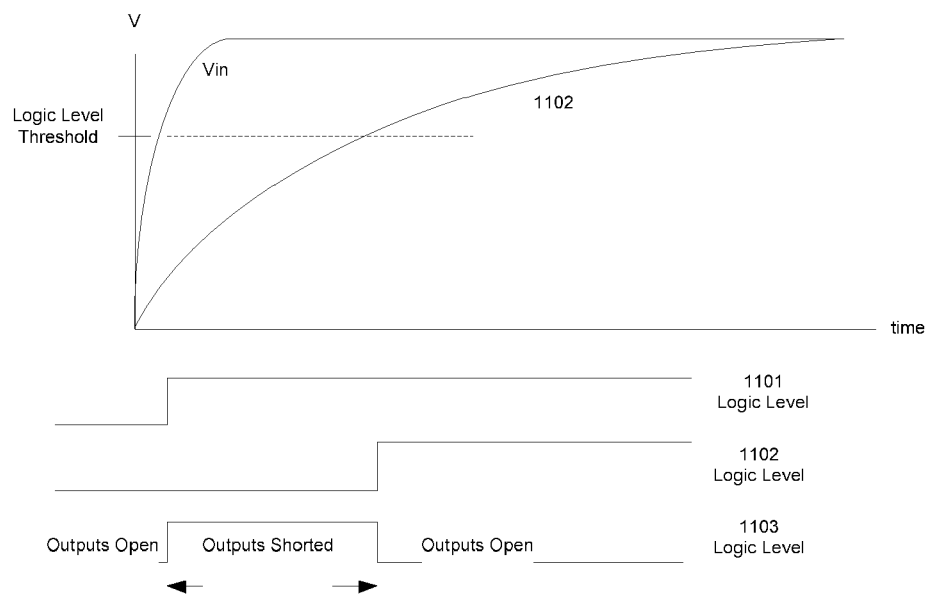

Another embodiment of the glitch generator 1000 is shown in FIGS. 11A-B. This implementation uses the rise of Vin as the timing for the start of the short-circuit. This glitch generator 1000 comprises a resistor 1001, a capacitor 1002, an XOR gate 1003, and a field-effect transistor (FET) 807. The FET 807 may be a JFET, MOSFET or any other form of FET. Initially the logic levels at 1101, 1102, and 1103 are low. At this point the electrical output is not shorted. After a specified time from the input of acoustic energy to the receiver-stimulator, voltage at 1101 crosses the logic level threshold and the logic level at 1101 becomes high. The logic level at 1102 is still low. The logic level at 1103 is now high and the electrical output is shorted. After another specified time the voltage at 1102 crosses the logic level threshold and the logic level at 1106 becomes high. At this point the logic level of 1103 returns to low and the short opens.

Various components of the glitch generators, such as the resistors and capacitors, may be varied in order to create unique glitch timing. Additionally, various components of the glitch generator may comprise capacitors with parallel resistors to quicken their discharge to ensure the time from one incoming interval to the next is long enough that the glitch generator circuitry has returned to its original state.

Although various embodiments as described herein are related to a leadless tissue stimulation system wherein an implantable or external controller-transmitter module generates acoustic waves of sufficient amplitude and frequency and for a duration and period such that a receiver-stimulator module receiving said acoustic waves may convert the acoustic energy into electric energy, it is contemplated that present devices, systems, and methods may be practiced without any acoustic transmission and conversion capabilities. In fact, present devices, systems, and methods may be implemented to locate, identify, and/or communicate with any implantable device that generates an electrical output that is detectable by any implantable or external controller. Alternatively and additionally, other forms of wireless energy in addition to acoustic energy may be used as the communication medium such as electromagnetic field energy.

While the above is a complete description of the preferred embodiments of the invention, various alternatives, modifications, and equivalents may be used. Therefore, the above description should not be taken as limiting the scope of the invention, which is defined by the appended claims.

What is claimed is:

1. A method of locating wireless implantable devices, comprising:
   generating an electrical stimulation output by an implantable device;
   modifying the electrical stimulation output with a glitch generated by a glitch generator located within the implantable device, wherein the glitch generator generates the glitch by modifying the electrical stimulation output and wherein the modifying occurs at a pre-configured interval;
   using a sensor of another device to sense the glitch that is incorporated within the modified electrical stimulation output; and
   wherein the modifying comprises shorting the electrical stimulation output.

2. The method of claim 1, further comprising determining the state of the implantable device based on characteristics of the sensed glitch.

3. The method of claim 1, further comprising sending a locator signal to the implantable device, whereupon receiving the locator signal, the implantable device generates the output modified by the glitch.

4. The method of claim 1, wherein the implantable device is an acoustic receiver-stimulator configured to receive acoustic energy and convert the acoustic energy to an electrical stimulation output.

5. The method of claim 4, wherein the receiver-stimulator comprises at least two electrodes configured to transmit the electrical stimulation output to a body region.

6. The method of claim 4, wherein the sensor is in or on an implantable controller-transmitter configured to transmit acoustic energy to the receiver-stimulator.

7. The method of claim 6, wherein the pre-configured interval occurs after the receiver-stimulator receives the acoustic energy generated by the controller-transmitter.

8. The method of claim 1, further comprising generating a second electrical stimulation output by a second implantable device, modifying the second electrical stimulation output with a second glitch generated by a second glitch generator within the second implantable device, wherein the second glitch generator generates the second glitch by modifying the second electrical stimulation output and wherein the modifying occurs at a second pre-configured interval; and using the sensor to detect the second glitch incorporated within the second modified electrical stimulation output.

9. The method of claim 8, further comprising using the sensor to distinguish between the first glitch and the second glitch.

10. The method of claim 9, further comprising using the sensor to select one of the two implantable devices based on the distinguished glitches; and sending a stimulation signal to the selected implantable device; wherein the stimulation signal causes the selected implantable device to deliver a third electrical stimulation output.

11. The method of claim 9, wherein the distinguishing comprises analyzing presence, absence, or timing information of the first glitch and the second glitch.

12. The method of claim 1, further comprising determining the location of the implantable device based on the detected glitch.

13. The method of claim 1, further comprising determining the identity of the implantable device based on the detected glitch.

14. The method of claim 1, wherein the glitch generator comprises a switch in series with one or more output electrodes configured to transmit the electrical stimulation output.

15. The method of claim 14, wherein the modifying comprises opening the switch to allow the voltage to rise without a load to power a timing circuitry within the implantable device.

16. An implantable device, comprising:
    at least two electrodes to deliver an electrical stimulation output to the body; and
    a glitch generator configured to modify the electrical stimulation output with a glitch, wherein the modifying occurs at a pre-configured interval, and wherein the glitch generator is configured to short the electrical stimulation output;
    wherein the modified electrical stimulation output is configured to be sensed by a separate controller-transmitter.

17. The device of claim 16, further comprising an acoustic transducer configured to receive acoustic energy and convert the acoustic energy to electrical energy.

18. The device of claim 17, wherein the controller-transmitter is implantable and is configured to transmit acoustic energy to the implantable device.

19. The device of claim 16, wherein the glitch communicates state information of implantable device using presence, absence, or timing information.

20. The device of claim 16, wherein the implantable device is configured to receive a locator signal generated by the controller-transmitter, and upon receiving the locator signal, the implantable device generates the output modified by the glitch.

21. The device of claim 20, wherein the implantable device is configured to receive a signal generated by the controller-transmitter, and upon receiving the signal, the implantable device generates an unmodified electrical output that is not modified by the glitch generator.

22. The device of claim 16, wherein the glitch generator comprises a switch in series with the at least two electrodes.

23. The device of claim 22, wherein the modifying comprises opening the switch to allow the voltage to rise without a load to power a timing circuitry within the implantable device.

24. A system for locating implantable devices, comprising:
- an implantable device, wherein the implantable device comprises at least two electrodes configured to transmit an electrical stimulation output to the body and a glitch generator configured to modify the electrical stimulation output with a glitch, wherein the modifying occurs at a pre-configured interval, and wherein the glitch generator is configured to short the electrical stimulation output;
- a controller-transmitter, wherein the controller-transmitter comprises at least one sensor configured to detect the glitch generated by the implantable device and a processor configured to analyze the glitch.

25. The system of claim 24, wherein the implantable device further comprises an acoustic transducer configured to receive acoustic energy and convert it into electrical energy.

26. The system of claim 25, wherein the controller-transmitter is configured to transmit acoustic energy to the implantable device.

* * * * *